(12) United States Patent
Peglion et al.

(10) Patent No.: US 6,399,616 B1
(45) Date of Patent: Jun. 4, 2002

(54) PYRIDINE COMPOUNDS

(75) Inventors: Jean-Louis Peglion, Le Vesinet; Aimée Dessinges, Rueil Malmaison; Christophe Poitevin, Paris; Mark Millan, Le Pecq; Anne Dekeyne, Saint Remy les Chevreuses, all of (FR)

(73) Assignee: Les Laboratoires Servier, Neuilly-sur-Seine (FR)

( * ) Notice: Subject to any disclaimer, the term of this patent is extended or adjusted under 35 U.S.C. 154(b) by 0 days.

(21) Appl. No.: 09/641,777

(22) Filed: Aug. 18, 2000

(30) Foreign Application Priority Data

Aug. 27, 1999 (FR) .............................. 99 10834

(51) Int. Cl.$^7$ .................. A61K 31/496; C07D 491/048; C07D 495/04
(52) U.S. Cl. .................. 514/253.04; 544/362; 546/114; 546/115; 514/301; 514/302
(58) Field of Search ...................... 544/362; 514/253.04

(56) References Cited

U.S. PATENT DOCUMENTS

| 5,001,130 | A | * | 3/1991 | New et al. .................. 544/295 |
| 5,681,954 | A | * | 10/1997 | Yamamoto et al. ......... 544/114 |
| 6,340,759 | B1 | * | 1/2002 | Ueno et al. ................. 514/301 |

OTHER PUBLICATIONS

Psychopharmacology (1997) 129: 197–205, Sanchez et al.
Psychopharmacology (1996) 123: 182–186, Hashimoto et al.
Psychopharmacology (1993) 112: 195–198, Woods et al.
Pharmacology Biochemistry and Behavior, vol. 52, No. 2, pp. 341–346 (1995), Meneses et al.
British Journal of Psychiatry (1998) 173 (supp 35), 64–70, Greist et al.
Neuroscience and Behavioral Reviews (1999) 23:1111–1125, Meneses.
European Journal of Pharmacology (1995) 283:133–139 , Carli et al.
European Journal of Pharmacology (1994) 261:321–325, Rodgers et al.
Japanese Journal of Pharmacology (1998) 76:297–304, Abe et al.
British Journal of Pharmacology (1999) 128:1207–1214, Carli et al.
Neuroscience Letters (1997) 229:204–208, Hasbroucq et al.
Journal of Pharmacology and Experimental Therabputics (1997) 282:148–161, Millan et al.
Psychopharmacology (2000) 152:55–66, Dekeyne et al.
Journal of Clinical Psychopharmacology (1999) vol. 19, No. 2:172–176, Kronig et al.
Psychopharmacology (1998) 135:383–391, Schreiber et al.
European Neuropsychopharmacology (2000) 10 (supp 4): S433–S437, Nutt.

* cited by examiner

*Primary Examiner*—Emily Bernhardt
(74) *Attorney, Agent, or Firm*—The Firm of Hueschen and Sage; G. Patrick Sage

(57) ABSTRACT

A compound selected from those of formula (I):

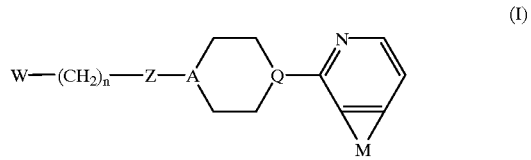

wherein:

W represents optionally substituted naphthyl, n represents an integer from 2 to 3 inclusive, Z represents a single bond, A represents nitrogen, Q represents nitrogen, M, together with the carbon of pyridyl to which it is bonded, represents thieno, furo, pyrrolo or oxopyrrolo, Its optical isomers and pharmaceutically-acceptable acid or base additional salts thereof, and Medicinal products containing the same which are useful in the treatment of CNS disorders.

It being understood that "aryl" is phenyl, naphthyl, dihydronaphthyl, or tetrahydronaphthyl.

12 Claims, No Drawings

PYRIDINE COMPOUNDS

FIELD OF THE INVENTION

The compounds of the present invention can be used in the treatment of disorders resulting from problems of which the cause lies in the central serotonergic system and which are known to be mediated in the reuptake of serotonin and/or at the level of 5-$HT_{1A}$ receptors, such as anxiety, panic attacks, obsessive-compulsive disorders, impulsive disorders, cognitive disorders, phobias and depression.

Regarding the treatment of depression, selective serotonin reuptake inhibitors (SSRI) currently represent one of the most effective classes of medicaments. Their beneficial therapeutic effects, however, do not become apparent before the end of the second week of treatment at the minimum, and most of the time do not become apparent until during the third or even the fourth week. This major drawback is damaging to the efficacy of that class of products. The latent period can be explained by the desensitisation of the 5-$HT_{1A}$ receptors of the cell bodies. Indeed it has been demonstrated (TIPS, 1993, 14, 262) that the efficacy of an SSRI such as fluoxetine may be reduced by the activation of 5-$HT_{1A}$ receptors, that activation resulting in a reduction in the discharge frequency of serotonergic neurons.

Consequently, a blockade of 5-$HT_{1A}$ receptors could lead to a more effective treatment (by reducing the latent period). Recently, a clinical study carried out with a partial 5-$HT_{1A}$ agonist *Clin. Psychopharmacol.*, 1995, 15, 217) demonstrated that such a substance may improve the efficacy of a concomitantly administered SSRI and/or may result in a reduction in the time taken for a concomitantly administered SSRI to take effect.

In vitro and in vivo experiments have made it possible to demonstrate that the compounds of the present invention combine a selective inhibitory-type activity in respect of the reuptake of serotonin (SSRI) with a partial agonist or antagonist activity in respect of 5-$HT_{1A}$ receptors. Thus, owing to their specific pharmacological activity, in addition to the fact that the compounds of the present invention are new, they may be useful in the treatment of anxiety, depression, panic attacks, obsessive-compulsive disorders, phobias, impulsive disorders and cognitive disorders.

PRIOR ART DESCRIPTION

Compounds of similar structures have already been described in the literature. This applies especially to the Patent Applications FR 2 738 822 and FR 2 738 823, which claim, in particular, compounds having a 4-(1-piperazinyl) thieno[3,2-c]pyridine moiety. Those compounds are useful in the treatment of hypertension, cardiac insufficiency, arthritis and microcirculation disorders. The Patent U.S. Pat. No. 4,677,104 claims compounds having either a 4-(1-piperazinyl)thieno, or furo, or 1H-pyrrolo[3,2-c]pyridine moiety, or a 7-(1-piperazinyl)thieno, or furo, or 1H-pyrrolo[2,3-c]pyridine moiety, those compounds being useful as antipsychotic or anxiolytic agents. Those compounds are substantially distinguished from the compounds described in the present invention by the presence of a very different ring system substituted on the piperazinyl moiety.

DETAILED DESCRIPTION OF THE INVENTION

The present invention relates more especially to compounds of formula (I):

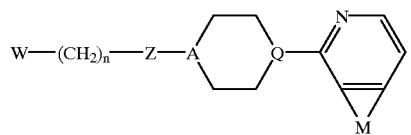

wherein:

W represents:
either a naphthyl group optionally substituted by one or more identical or different groups selected from halogen, linear or branched ($C_1$-$C_6$)alkyl, hydroxy, linear or branched ($C_1$-$C_6$)alkoxy, cyano, nitro, linear or branched trihalo($C_1$-$C_6$)alkyl, methylenedioxy and ethylenedioxy, or a group of formula Y where:

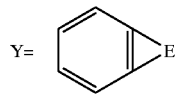

wherein E, together with the carbon atoms of the phenyl ring to which it is bonded, represents an unsaturated, partially saturated, or aromatic, monocyclic ring having from 5 to 7 ring members and containing at least one hetero atom selected from oxygen, nitrogen and sulphur, it being possible for the said group Y to be bonded to the $(CH_2)_n$ group of the compounds of formula (I) either by the phenyl moiety or by the monocyclic ring E, and for each of the said Y groups to be optionally substituted by one or more identical or different groups selected from halogen, hydroxy, cyano, nitro, linear or branched ($C_1$-$C_6$)alkyl, linear or branched ($C_1$-$C_6$) alkoxy, linear or branched trihalo($C_1$-$C_6$)alkyl, heterocycloalkylalkylene in which the alkylene moiety contains from 1 to 6 carbon atoms and may be linear or branched (and in which the heterocyclic ring is an unsaturated or aromatic monocyclic ring having 5 or 6 ring members and containing from 1 to 4 hetero atoms selected from nitrogen, sulphur and oxygen) and oxo, provided that in that case the group Y can be substituted only by a single oxo group and that E, together with the carbon atoms of the phenyl ring to which it is bonded, represents then a monocyclic ring having 5 ring members and containing two identical or different hetero atoms selected from oxygen and nitrogen, n represents an integer from 1 to 6 inclusive, Z represents a single bond, an oxygen atom, or a nitrogen atom substituted by a group selected from hydrogen, linear or branched ($C_1$-$C_6$)alkyl (itself optionally substituted by one or more hydroxy groups) and aryl-($C_1$-$C_6$)alkyl in which the alkyl moiety may be linear or branched, A represents a CH group or a nitrogen atom, Q represents a CH group or a nitrogen atom, provided that at least one of the groups A and Q represents a nitrogen atom, and that A represents a nitrogen atom when Z represents a single bond, and M, together with the carbon atoms of the pyridyl ring to which it is bonded, represents a thieno, furo, pyrrolo or oxopyrrolo group, to their isomers, and to addition salts thereof with a pharmaceutically acceptable acid or base.

"Aryl" is to be understood as meaning a phenyl, naphthyl, dihydronaphthyl or tetrahydronaphthyl group.

Advantageously, preferred W substituents of the invention are the groups naphthyl, 2,3-dihydro-1,4-benzodioxinyl, chromanyl, 2H-chromenyl, isochromanyl, 2,3-dihydrobenzofuranyl, benzofuranyl, 1,3-dihydro-2H-benzimidazol-2-one, 1,3-benzoxazol-2-one and indolyl.

where W is optionally subdued by a heterocycloalkylalkylene group in which the alkylene moiety is linear or branched and contains from 1 to 6 carbon atoms, the said heterocycloalkylalkylene group is advantageously a heterocycloalkylmethylene group in which heterocycloalkyl is an unsaturated or aromatic monocyclic ring having 5 ring members and containing from 1 to 4 nitrogen atoms. Preferably, the said heterocycloalkylmethylene group is a 1,2,4-triazol-1-ylmethyl, imidazol-1-ylmethyl or 1H-imidazol-5-ylmethyl group.

In an especially advantageous embodiment, the substituents W preferred in accordance with the invention are the groups 1-naphthyl, isochroman-1-yl and 2,3-dihydro-1-benzofuran-5-yl.

In another especially advantageous embodiment, the substituents W preferred in accordance with the invention are the 5-(1,2,4-triazol-1-ylmethyl)-1H-indol-3-yl group, the 5-(imidazol-1-ylmethyl)-1H-indol-3-yl group and the 5-(1H-imidazol-5-ylmethyl)-1H-indol-3-yl group.

In a third especially advantageous embodiment, the substituents W preferred in accordance with the invention are the groups 1,3-benzoxazol-2-on-1-yl and 1,3-dihydro-2H-benzimidazol-2-on-1-yl.

Preferably, Z represents a single bond in the compounds of the invention.

According to a valuable embodiment, preferred compounds of the invention are compounds of formula (I) wherein Z represents a nitrogen atom substituted by a group selected from hydrogen, methyl and hydroxyethylene when A presents a CH group, Q represents a nitrogen atom, n is 1 and W represents a 2-naphthyl group.

According to an advantageous embodiment of the invention, preferred compounds are those wherein n represents 2 or 3.

According to another advantageous embodiment of the invention, preferred compounds are those wherein M, together with the carbon atoms of the pyridyl ring to which it is bonded represents a thieno or furo group.

Preferred compounds of the invention are especially advantageously:
4-{1-[2-(1-naphthyl)ethyl]-4-piperidinyl}thieno[3,2-c]pyridine,
4-{1-[2-(1-naphthyl]-4-piperidinyl}furo[3,2-c]pyridine,
4-{4-[2(2,3-dihydrobenzofuran-5-yl)ethyl]-1-piperazinyl}furo[3,2-c]pyridine,
4-{4-[2-(isochroman-1-yl)ethyl]-1-piperazinyl}furo[3,2-c]pyridine,
4-(4-{2-[5-(1,2,4-triazol-1-ylmethyl)-1H-indol-3-yl]ethyl}-1-piperazinyl)furo[3,2-c]pyridine,
4-(4-{2-[5-(1,2,4-triazol-1-ylmethyl)-1H-indol-3-yl]ethyl}-1-piperazinyl)-1H-pyrrolo[3,2-c]pyridine,
1-[2-(4-furo[3,2-c]pyridin-4-yl-1-piperazinyl)ethyl]-1,3-dihydro-2H-benzimidazol-2-one,
and 1-[2-(4-thieno[3,2-c]pyridin-4-yl-1-piperazinyl)ethyl]-1,3-dihydro-2H-benzimidazol-2-one, The isomers, and also the addition salts with a pharmaceutically acceptable acid or base, of the preferred compounds form an integral part of the invention.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid, etc.

Among the pharmaceutically acceptable bases there may be mentioned, without implying any limitation, sodium hydroxide, potassium hydroxide, triethylamine, tert-butylamine, etc.

The invention extends also to a process for the preparation of the compounds of formula (I), which is characterised in that there is used as starting material a compound of formula (II):

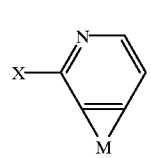

(II)

wherein M is as defined for formula (I) and X represents a chlorine, bromine or iodine atom or a leaving group, such as mesyl, tosyl or triflyl,
which compound of formula (II) is reacted in the presence of a base with a compound of formula (III):

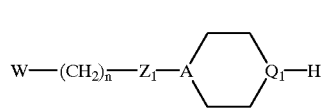

(III)

wherein W, n and A are as defined for formula (I), $Q_1$ represents a nitrogen atom and $Z_1$ represents a single bond, an oxygen atom or an NH group,
to yield the compounds of formula (I/a), a particular case of the compounds of formula (I):

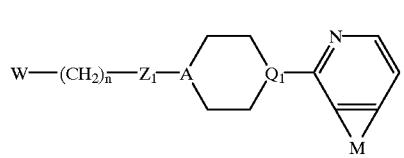

(I/a)

wherein W, n, $Z_1$, A, M and $Q_1$ are as defined hereinbefore,
* or which compounds of formula (II) are converted, in accordance with the conventional conditions of organic synthesis, into compounds of formula (IV):

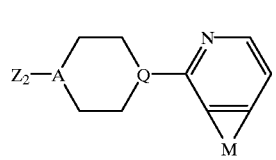

(IV)

wherein A, Q and M are as defined for formula (I), and $Z_2$ represents a hydrogen atom when A represents a nitrogen atom or $Z_2$ represents an $NH_2$ group when A represents a CH group,
which compounds of formula (IV) are reacted,
either with a compound of formula (V):

$$W-(CH_2)_{n-1}-CO_2H \qquad (V)$$

wherein W and n are as defined for formula (I), in the presence of a coupling agent,
to yield the compounds of formula (VI):

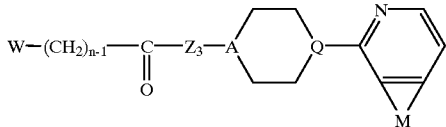

wherein W, n, A, Q and M are as defined for formula (I), and $Z_3$ represents a bond when A represents a nitrogen atom or $Z_3$ represents an NH group when A represents a CH group, which compounds of formula (VI) are treated with a reducing agent, in accordance with conventional conditions of organic synthesis, to yield the compounds of formula (I/b), a particular case of the compounds of formula (I):

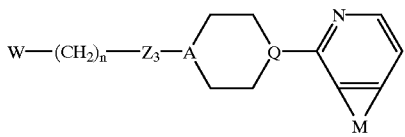

wherein W, n, A, Q, M and $Z_3$ are as defined hereinbefore,
or with a compound of formula (VII):

wherein W and n are as defined hereinbefore, under reductive amination conditions,
to yield, directly, the compounds of formula (I/b) as defined hereinbefore,
or with a compound of formula (VIII):

wherein W and n are as defined hereinbefore and X represents a chlorine, bromine or iodine atom or a leaving group, such as tosyl, mesyl or triflyl, in the presence of a phase transfer agent or a base,
also to yield, directly, the compounds of formula (I/b) as defined hereinbefore,
the compounds of formulae (I/a) and (I/b) constituting the compounds of formula (I/c):

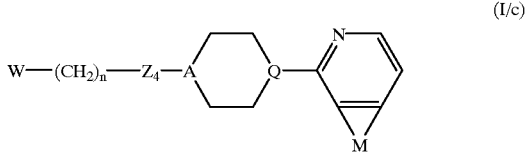

wherein W, n, A, Q and M are as defined for formula (I) and $Z_4$ represents a bond, an oxygen atom or an NH group,
which compounds of formula (I/c), when $Z_4$ is $Z'_4$ and represents an NH group, and A is $A_1$ and represents a CH group, are subjected to an alkylation reaction according to conventional methods of organic synthesis to yield the compounds of formula (I/d), a particular case of the compounds of formula (I):

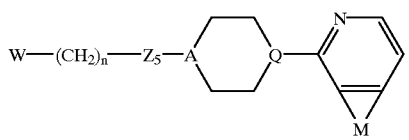

wherein W, n, Q, M and $A_1$ are as defined hereinbefore and $Z_5$ represents a nitrogen atom substituted by a linear or branched ($C_1$–$C_6$)alkyl group (itself optionally substituted by one or more hydroxy groups) or by aryl-($C_1$–$C_6$)alkyl in which the alkyl moiety may be linear or branched,
the compounds (I/a) to (I/d) constituting the totality of the compounds of the invention, which compounds are purified, if necessary, according to conventional purification techniques, are separated, if desired, into their isomers according to a conventional separation technique, and are converted, if desired, into addition salts with a pharmaceutically acceptable acid or base.

The compounds of formulae (II), (III), (V), (VII) and (VIII) are either commercially available compounds or compounds obtained according to conventional methods of organic synthesis.

The present invention extends also to pharmaceutical compositions comprising as active ingredient at least one compound of formula (I), an isomer thereof or an addition salt thereof with a pharmaceutically acceptable acid or base, alone or in combination with one or more pharmaceutically acceptable, inert, non-toxic excipients or carriers.

Among the pharmaceutical compositions according to the invention there may be mentioned more especially those which are suitable for oral, parenteral (intravenous, intramuscular or subcutaneous) per- or trans-cutaneous, nasal, rectal, perlingual, ocular or respiratory administration, and especially tablets or dragées, sublingual tablets, soft gelatin capsules, hard gelatin capsules, suppositories, creams, ointments, dermal gels, injectable or drinkable preparations, aerosols, eye or nose drops, etc.

In view of the selective inhibitory activity in respect of serotonin reuptake and the 5-HT$_{1A}$ receptor partial agonist or antagonist activity of the compounds of the invention, the pharmaceutical compositions comprising as active ingredient at least one compound of the invention are useful in the treatment of depression, anxiety, panic attacks, obsessive-compulsive disorders, phobias, impulsive disorders and cognitive disorders.

The useful dosage varies in accordance with the the age and weight of the patient, the route of administration, the nature and severity of the disorder and the administration of possible associated treatments and ranges from 0.5 to 50 mg in one or more administrations per day.

The following Examples illustrate the invention but do not limit it in any way.

The starting materials employed are either known products or are products prepared according to known procedures.

The various preparation procedures result in synthesis intermediates for use in the preparation of the compounds of the invention.

The structures of the compounds described in the Examples and in the Preparation Procedures were determined according to customary spectrophotometric techniques (infra-red, nuclear magnetic resonance, mass spectrometry . . . ). The melting points were determined using a Kofler hot plate (B.K.) or a hot plate under microscope (M.K.).

PREPARATION 1

4-[(Trifluoromethyl)sulfonyl]furo[3,2-c]pyridine 2.1 equivalents of triflic anhydride in 10 ml of dichloromethane are added dropwise to a solution, cooled to −78° C., of 14.8 mmol of furo[3,2-c]pyridin-4(5H)-one (*J. Med. Chem.*, 1989, 32, 1147–1156) and 2.1 equivalents of pyridine in 80 ml of dichloromethane. The reaction is continued for 1 hour at −78° C., then brought to ambient temperature for 12 hours. After hydrolysis of the reaction mixture by the addition of 20 ml of water, then extraction with dichloromethane, the organic phase is dried and filtered and then concentrated under reduced pressure. Chromatography on silica gel (dichloromethane) enables the expected product to be isolated.

PREPARATION 2

4-[(Trifluoromethyl)sulfonyl]thieno[3,2-c]pyridine

The procedure is as in Preparation 1, using as substrate thieno[3,2-c]pyridin-4(5H)-one.

Melting point: 110–112° C. (B.K.).

PREPARATION 3

4-(1-Piperazinyl)furo[3,2-c]pyridine

A solution of 0.065 mol of 4-chlorofuro[3,2-c]pyridine and 5 equivalents of piperazine in 25 ml of ethanol is heated for 17 hours at 120° C. under an inert atmosphere. After cooling and concentration under reduced pressure, the residue obtained is stirred in the presence of 150 ml of water and 150 ml of dichloromethane. After decanting and extraction with dichloromethane, the organic phases are dried and filtered and then concentrated under reduced pressure, enabling the expected product to be isolated.

Melting point: 90–92° C. (B.K.).

PREPARATION 4

7-(1-Piperazinyl)thieno[2,3-c]pyridine

The procedure is as in Preparation 3, using as substrate 7-chlorothieno[2,3-c]pyridine.

PREPARATION 5

7-(1-Piperazinyl)furo[2,3-c]pyridine

The procedure is as in Preparation 3, using as substrate 7-chlorofuro[2,3-c]pyridine.

Melting point: 60–65° C. (B.K.).

PREPARATION 6

4-(1-Piperazinyl)thieno[3,2-c]pyridine

The procedure is as in Preparation 3, using as substrate 4-chlorothieno[3,2-c]pyridine.

Melting point: 95–100° C. (B.K.).

PREPARATION 7

4-(4-Piperidinyl)furo[3,2-c]pyridine

Step A: 1-Acetyl-4-hydroxy-4-(tributylstannyl)piperidine

Under an inert atmosphere, 0.32 mmol of n-butyllithium (1.6M in hexane) is added over a period of 5 minutes to a solution of 0.32 mmol of diisopropylamine in 750 ml of tetrahydrofuran at 0° C. After stirring the mixture for 15 minutes, 0.32 mmol of tri-n-butyltin hydride is added. After 1 hour 30 minutes at 0° C., the reaction mixture is cooled to −70° C. and 0.26 mmol of N-acetylpiperidone in 225 ml of tetrahydrofuran is added and the reaction mixture is then diluted by adding 380 ml of tetrahydrofuran. After stirring for 2 hours 30 minutes, the reaction mixture is hydrolysed by the addition of 200 ml of an aqueous 10% solution of $NaH_2PO_4$, brought to 0° C., and then diluted with 2 litres of ether and 1 litre of water. After decanting and washing with a saturated NaCl solution, the organic phase is dried and filtered and then concentrated under reduced pressure. Chromatography on silica gel (dichloromethane) enables the expected product to be isolated.

Step B: 1-Acetyl-1,2,3,6-tetrahydro-4-tributylstannyl-pyridine

Under an inert atmosphere, 1.3 equivalents of mesyl chloride in 15 ml of dichloromethane are added dropwise to a solution of 0.16 mmol of the compound obtained in Step A and 2.8 equivalents of triethylamine in 1 litre of dichloromethane at 0° C. After stirring the mixture at ambient temperature for 4 days, a saturated aqueous solution of NaCl is added. After extraction, drying, filtration and concentration of the organic phase under reduced pressure, chromatography of the residue on silica gel (dichloromethane/ethanol: 97/3) enables the expected product to be isolated.

Step C: 4-(1-Acetyl-1,2,3,6-tetrahydropyridin-4-yl)furo[3,2-c]pyridine 7 equivalents of LiCl, and then 0.03 equivalents of $Pd(PPh_3)_4$ are added, under a stream of argon, to a solution of 52.3 mmol of the product of Preparation 1 and 1.2 equivalents of the product obtained in Step B in 800 ml of dioxane. The reaction mixture is heated to 100° C. and 0.03 equivalent of $Pd(PPh_3)_4$ is added in succession, after reaction for 12 hours, 24 hours and 48 hours, and the reaction mixture is maintained at 100° C. for an additional 24 hours. After cooling, filtration over Celite and concentration under reduced pressure, chromatography of the residue on silica gel (dichloromethane/ethanol: 97/3) enables the expected product to be isolated; the product is then crystallised in pentane.

Melting point: 128–130° C. (B.K.).

Step D: 4-(1-Acetylpiperidin-4-yl)furo[3,2-c]pyridine 0.7 g of Pd/C (10%) is added to a solution of 3.4 g of the product obtained in Step C and 4.4 g of ammonium formate in 150 ml of anhydrous methanol under a stream of argon. After refluxing for 45 minutes, the reaction mixture is cooled, 4.4 g of ammonium formate 5 and 0.2 g of Pd/C (10%) are added, and the reaction mixture is then heated at reflux for 30 minutes. After returning to ambient temperature, filtration over Celite and concentration under reduced pressure, the residue is taken up in water and then extracted with dichloromethane. The expected product is isolated by extraction, drying, filtration and concentration under reduced pressure.

Melting point: 108–110° C. (B.K.).

Step E: 4-(4-Piperidinyl)furo[3,2-c]pyridine

A solution of 2.7 g of the product obtained in Step D in 80 ml of HCl (4N) is heated at 100° C. for 12 hours and then cooled, washed with ether, and rendered basic to a pH of 10 by the addition of an aqueous sodium hydroxide solution. After extraction with dichloromethane, the organic phase is dried, filtered and then evaporated to dryness enabling the expected product to be obtained.

PREPARATION 8

4-(4-Piperidinyl)thieno[3,2-c]pyridine

Step A: 2-(2-Nitroethyl)thiophene 15.7 g of silica 60 (230–400 mesh) and then 2.95 g of NaBH$_4$ are added to a solution of 32.2 mmol of 2-(2-nitrovinyl)thiophene in 210 ml of chloroform and 70 ml of isopropanol. After stirring the mixture for one hour at ambient temperature, 5 ml of acetic acid are added dropwise and then, after 15 minutes, the resulting suspension is filtered and subsequently rinsed with dichloromethane. Concentration of the filtrate under reduced pressure enables the expected product to be isolated.

Step B: 2-(2-Aminoethyl)thiophene 0.5 g of platinum oxide is added to 42 g of the product obtained in Step A in 400 ml of methanol, and then the reaction mixture is placed under a stream of hydrogen at ambient temperature. After 6 hours, filtration over Celite followed by evaporation enables the expected product to be isolated.

Step C: 1-Benzyl-N-[2-(2-thienyl)ethyl]-4-piperidinecarboxamide 22.15 g of ethyl 1-benzyl-4-piperidinecarboxylate and 1 equivalent of the product obtained in Step B are added to a solution of 4.12 g of sodium in 103 ml of anhydrous ethanol. After 12 hours reaction at reflux, the reaction mixture is evaporated. The residue is taken up in dichloromethane and washed with water, and then the organic phase is dried, filtered and evaporated, enabling an oil to be obtained which crystallises in diisopropyl ether.

Step D: 4-(1-Benzyl-4-piperidinyl)-6,7-dihydro-thieno[3,2-c]pyridine

A solution of 2 g of the product obtained in Step C in 8 ml of toluene, and 12 mmol of POCl$_3$, are heated at reflux. After 4 hours, the reaction mixture is poured onto ice, rendered basic by the addition of a 20% sodium hydroxide solution and then extracted with dichloromethane. The organic phase is dried and filtered and then evaporated, enabling the expected product to be isolated.

Step E: 4-(1-Benzyl-4-piperidinyl)thieno[3,2-c]pyridine 6.5 g of the compound obtained in Step D and 0.3 g of Pd/C (5%) are heated for 40 minutes at 220–240° C. under nitrogen, and then 0.3 g of Pd/C is added again and the reaction is continued for 50 minutes. After returning to ambient temperature, taking up in ethanol, filtration over Celite and concentration under reduced pressure, chromatography of the residue on silica gel (dichloromethane/methanol: 95/5) enables the expected product to be isolated.

Step F: Ethyl 4-thieno[3,2-c]pyridin-4-yl-1-piperidinecarboxylate 1 g of the product obtained in Step E is added dropwise to a suspension of 93 ml of ethyl chloroformate and 0.89 g of K$_2$CO$_3$ in 5 ml of toluene. After 12 hours at ambient temperature, the reaction mixture is diluted with water, extracted with toluene and then concentrated under reduced pressure. Chromatography on silica gel (dichloromethane/methanol: 95/5) enables the expected product to be isolated.

Step G: 4-(4-Piperidinyl)thieno[3,2-c]pyridine

A solution of 0.57 g of the product obtained in Step F in 4 ml of HCl (5N) is heated at reflux for 12 hours and then cooled, washed with ether, rendered basic by the addition of 20% sodium hydroxide solution and extracted with dichloromethane. Drying, filtration and concentration of the organic phase under reduced pressure, followed by chromatography on silica gel (CH$_2$Cl$_2$/MeOH/NH$_4$OH: 90/10/1), enables the expected product to be isolated.

PREPARATION 9

4-(4-Aminopiperidin-1-yl)thieno[3,2-c]pyridine hydrochloride

Step A: tert-Butyl 4-piperidinylcarbamate 6 g of Pd/C (10%) are added to a solution of 0.224 mol of tert-butyl 1-benzyl-4-piperidinylcarbamate in 800 ml of anhydrous ethanol. The reaction mixture is placed under a hydrogen pressure of 4 bars, at 50° C., for 48 hours, and then filtered over Celite and concentrated under reduced pressure, enabling the expected product to be isolated.

Melting point: 154–156° C. (B.K.).

Step B: tert-Butyl 1-thieno[3,2-c]pyridin-4-yl-piperidinylcarbamate

A solution of 5.65 g of the product obtained in Step A and 1 equivalent of the product of Preparation 2 in DMSO is heated at 50° C. for 2 hours, then poured onto ice and extracted with ethyl acetate. After washing with water, the organic phase is dried and filtered and then evaporated. Chromatography on silica gel (dichloromethane/methanol: 90/10) enables the expected product to be isolated.

Step C: 4-(4-Aminopiperidin-1-yl)thieno[3,2-c]pyridine hydrochloride

A stream of gaseous HCl is injected into a solution of 5.4 g of the product obtained in Step B in 200 ml of ethyl acetate, and the temperature is increased to 50° C. for a few minutes. After returning the mixture to ambient temperature and stirring the mixture for 2 hours, the precipitate obtained is filtered off and rinsed with ethyl acetate, enabling the expected product to be isolated.

Melting point: >260° C. (B.K.).

PREPARATION 10

7-(1-Piperazinyl)-1,3-dihydro-2H-pyrrolo[2,3-c]pyridin-2-one

Step A: [2-(4-Benzyl-1-piperazinyl)-3-nitro-4-pyridinyl]acetonitrile

A solution of 15 g of (2-chloro-3-nitropyridin-4-yl)acetonitrile and 1.1 equivalents of N-benzyl-piperazine is heated for 10 minutes, at 80° C., under a stream of argon, and then concentrated under reduced pressure. Chromatography on silica gel (dichloromethane/methanol: 100/0 to 95/5) enables the expected product to be isolated.

Step B: [2-(4-Benzyl-1-piperazinyl)-3-amino-4-pyridinyl]acetonitrile 43 ml of hydrochloric acid and 35 g of iron powder are added to a suspension, that has been heated at 80° C. for 1 hour, of 59 mmol of the product obtained in Step A in 1.5 l of absolute ethanol. After 2 hours 30 minutes at 80° C., filtration while hot, and concentration of the reaction mixture under reduced pressure, the residue is taken up in water, rendered basic with a 20% sodium hydroxide solution and extracted with ethyl acetate. The organic phase is subsequently dried, filtered and evaporated, and chromatography of the residue on silica gel (dichloromethane/ethanol: 90/10) enables the expected product to be isolated.

Step C: 7-(4-Benzyl-1-piperazinyl)-1,3-dihydro-2H-pyrrolo[2,3-c]pyridin-2-one

A suspension of 9.2 g of the compound obtained in the above Step B in 300 ml of an aqueous 6N solution of hydrochloric acid is heated at reflux for 4 hours. After concentration under reduced pressure, the solid residue is dissolved with water and adjusted to a basic pH by 20% sodium hydroxide solution. The solution is extracted with ethyl acetate and then the organic phases are dried over magnesium sulfate and concentrated under reduced pressure to yield the expected product.

Melting point: 218–220° C. (M.K).

Step D: 7-(1-Piperazinyl)-1,3-dihydro-2H-pyrrolo[2,3-c]pyridin-2-one

A suspension of 1.9 g of the compound obtained in Step C in 250 ml of absolute ethanol is hydrogenated in the presence of 10% palladium-on-carbon (0.3 equivalent) at 50° C., under 1 bar, for 2 days. The catalyst is removed by filtration, and evaporation of the solvent under reduced pressure and purification yield the expected product.

Melting point: 200–204° C. (M.K.).

PREPARATION 11

7-(4-Amino-1-piperidinyl)-1,3-dihydro-2H-pyrrolo[2,3-c]pyridin-2-one

Step A: {2-[4-(tert-Butoxycarbonylamino)-1-piperidinyl]-3-nitro-4-pyridinyl}-acetonitrile The procedure is as in Step A of Preparation 10, using as substrate 4-(tert-butoxycarbonylamino)piperidine.

Melting point: 160–170° C.

Step B: {2-[4-tert-Butoxycarbonylamino)-1-piperidinyl]-3-amino-4-pyridinyl}acetonitrile 1.9 g of the product obtained in the above Step A are dissolved in 400 ml of methanol and then hydrogenated in the presence of 5% palladium-on-carbon for 8 hours at ambient temperature. The expected product is obtained in quantitative yield after filtration and evaporation.

Step C: 7-(4-Amino-1-piperidinyl)-1,3-dihydro-2H-pyrrolo[2,3-c]pyridin-2-one

The procedure is as in Step C of Preparation 10, but using the product obtained in the above Step B.

PREPARATION 12

7-(1-Piperazinyl)-1H-pyrrolo[2,3-c]pyridine 9.2 g of the compound obtained in Step A of Preparation 10, in 250 ml of absolute ethanol, are hydrogenated at 65° C. for 4 days under 3 bars in the presence of 5% palladium-on-carbon. After removal of the catalyst by filtration and removal of the solvent by evaporation, the residue is purified by chromatography on silica gel (dichloromethane/ethanol 100/0 to 95/0) to yield the expected product.

PREPARATION 13

7-(4-Amino-1-piperidinyl)-1H-pyrrolo[2,3-c]pyridine

Step A: 7-[4-(tert-Butoxycarbonylamino)-1-piperidinyl]-1H-pyrrolo[2,3-c]pyridine The procedure is as in Preparation 12, using as substrate the compound obtained in Step A of Preparation 11.

Step B: 7-(4-Amino-1-piperidinyl)-1H-pyrrolo[2,3-c]pyridine

A solution of 50 ml of 2.5N ethanolic HCl is added to a solution of 5.1 g of the product obtained in the above Step A in 100 ml of absolute ethanol. The resulting solution is stirred at ambient temperature for 16 hours. After concentration under reduced pressure, the residue is diluted with water, rendered alkaline with 20% sodium hydroxide solution and extracted with dichloromethane, and the organic phases are dried over magnesium sulfate and concentrated under reduced pressure to yield the expected product.

PREPARATION 14

4-(1-Piperazinyl)-1H-pyrrolo[3,2-c]pyridine and its Hydrochloride

Step 1: 1-Benzyl-4-bromo-1H-pyrrolo[3,2-c]pyridine 35 g of N-bromosuccinimide are added to a solution of 52 g of triphenylphosphine in 1.5 l of dioxane. After stirring the mixture for 1 hour, 9 g of 1-benzyl-1,5-dihydro-pyrrolo[3,2-c]pyridin-4-one in 200 ml of dioxane are added and the mixture is heated at reflux for 15 hours. After removal of the dioxane under reduced pressure, 100 ml of triethylamine are added to the residue and the whole is then concentrated in vacuo. Chromatography on silica gel (cyclohexane/ethyl acetate: 50/50) enables the expected product to be isolated.

Melting point: 95–100° C.

Step 2: 1-Benzyl-4-(1-piperazinyl)-1H-pyrrolo[3,2-c]pyridine

A solution of 4.5 g of 1-benzyl-4-bromo-1H-pyrrolo[3,2-c]pyridine in 25 ml of anhydrous ethanol and 8 g of piperazine are stirred at 120° C. for 15 hours under an inert atmosphere, then brought to ambient temperature and concentrated under reduced pressure. The residue is taken up in 200 ml of dichloromethane and washed with water. The organic phase is treated in conventional manner and then concentrated, enabling the expected product to be isolated.

Step 3: 4-(1-Piperazinyl)-1H-pyrrolo[3,2-c]pyridine and its dihydrochloride 4.1 g of the compound obtained in Step 2 dissolved in 75 ml of tetrahydrofuran and 1 g of sodium are added in succession to 190 ml of liquid ammonia at −75° C. After 35 minutes, 2.3 g of ammonium chloride are added and the ammonia is evaporated off. 20 ml of water are then added and, after stirring for 30 minutes, the solution is extracted with diethyl ether, dried, filtered and concentrated in vacuo. The residue is taken up in 25 ml of ethanol and 10 ml of 2.9N ethereal hydrogen chloride are added, and then the mixture is concentrated in vacuo. The solid obtained is stirred for 18 hours in 30 ml of ethyl acetate, resulting in the formation of a precipitate which enables the expected product to be isolated by filtration and washing with ethyl acetate.

Melting point: 320–325° C.

PREPARATION 15

4-(4-Piperidinyl)-1H-pyrrolo[3,2-c]pyridine

Step 1: tert-Butyl 4-hydroxy-1-piperidinecarboxylate 59 g of di-tert-butyl dicarbonate are added to a solution, cooled to −10° C., of 25 g of 4-hydroxypiperidine and 39 ml of triethylamine in 500 ml of dichloromethane while maintaining the temperature below 0° C. The mixture is stirred for 1 hour 30 minutes at a temperature below 15° C. and is then concentrated in vacuo. The residue is taken up in 500 ml of dichloromethane and washed with 200 ml of an aqueous 1N HCl solution. The expected product is isolated by treating in conventional manner and concentrating under reduced pressure.

Melting point: 55–60° C.

Step 2: tert-Butyl 4-iodo-1-piperidinecarboxylate 86 g of iodine are added at ambient temperature to a suspension of 89 g of triphenylphosphine and 22 g of imidazole in 800 ml of acetonitrile. The reaction is exothermic. After return to ambient temperature, 45.9 g of the product obtained in Step 1 in 250 ml of acetonitrile are added in the course of 30 minutes. After 18 hours stirring at ambient temperature, the reaction mixture is filtered and rinsed with 200 ml of acetonitrile and the resulting filtrate is concentrated in vacuo. The residue obtained is stirred in 250 ml of diethyl ether for 1 hour and the precipitate is filtered off. After concentration of the filtrate in vacuo, chromatography on silica gel (dichloromethane/ethyl acetate: 90/10) enables the expected product to be isolated.

Step 3: tert-Butyl 4-(1-benzyl-1H-pyrrolo[3,2-c]pyridin-4-yl)-1-piperidinecarboxylate 0.16 ml of 1,2-dibromoethane is added at ambient temperature, under argon, to a suspension of 1.35 g of powdered zinc in 10 ml of tetrahydrofuran. The mixture is heated for 5 minutes at 65° C., then brought to ambient temperature, and 0.23 ml of trimethylsilyl is then added. After stirring the mixture for 30 minutes, a solution of 4.5 g of the compound obtained in Step 2 in 8 ml of tetrahydrofuran is slowly added, and then after 45 minutes a solution, prepared ex situ 10 minutes beforehand, of 0.2 g of $Pd_2$(dba)$_3$ and 0.2 g of P(2-furyl)$_3$ in 5 ml of tetrahydrofuran is added by cannulation under argon and, finally, 5.5 g of 1-benzyl-4-bromo-1H-pyrrolo[3,2-c]pyridine in 30 ml of a 1/1 tetrahydrofuran/dimethylamine mixture are added. The reaction mixture is heated at 65° C. for 16 hours and then, after return to ambient temperature, filtered and concentrated in vacuo. Chromatography on silica gel (cyclohexane/ethyl acetate: 50/50) enables the expected product to be isolated.

Step 4: 1-Benzyl-4-(4-piperidinyl)-1H-pyrrolo[3,2-c]pyridine 15 ml of a 2.9N ethanolic HCl solution are added to a solution of 0.9 g of the compound obtained in Step 3 in 15 ml of ethanol. The reaction mixture is stirred for 24 hours at ambient temperature and then concentrated in vacuo, enabling the expected product to be isolated in dihydrochloride form. The dihydrochloride is converted into a free base by extraction in dichloromethane in the presence of water that has previously been adjusted to a basic pH by 20% sodium hydroxide solution.

Step 5: 4-(4-Piperidinyl)-1H-pyrrolo[3,2-c]pyridine

The procedure is as Step 3 of the Preparation 14, using as substrate the product obtained in the above Step 4.

EXAMPLE 1

1-Furo[2,3-c]pyridin-7-yl-N-(2-naphthylmethyl)-4-piperidinamine and its Fumarate 2.5 g of 4-(naphth-2-ylmethylamino)piperidine and 1,6 g of 7-chlorofuro[2,3-c]pyridine are dissolved in 10 ml of ethanol containing 3.6 ml of N,N-diisopropylethylamine, heated at reflux and then evaporated to dryness and chromatographed on silica gel (dichloromethane/ethanol: 95/5). An oil is obtained which crystallises; the oil is converted into the fumarate by the addition of a 2% fumaric acid solution in ethanol.

Melting point: 203–207° C. (M.K.) (fumarate).

EXAMPLE 2

7-[4-(2-Naphthylmethoxy)-1-piperidinyl]furo[2,3-c]pyridine

The procedure is as in Example 1, using as substrate 4-(2-naphthylmethoxy)piperidine.

Melting point: 74–77° C. (M.K.).

EXAMPLE 3

1-Furo[2,3-c]pyridin-7-yl-N-methyl-N-(2-naphthylmethyl)-4-piperidinamine

Step A: Ethyl N-(2-naphthylmethyl)-N-[1-(furo[2,3-c]pyridin-7-yl)piperidin-4-yl]-carbamate 0.3 ml of ethyl chloroformate in 20 ml of dichloromethane is added at 0° C. to a solution of 0.9 g of the compound of Example 1 in 50 ml of dichloromethane and 0.85 ml of triethylamine. After 48 hours at ambient temperature, dilution with dichloromethane and with water, extraction, drying and concentration under reduced pressure, chromatography on silica gel (dichloromethane/ethyl acetate 95/5) enables the expected product to be isolated.

Melting point: 118–120° C.

Step B: 1-Furo[2,3-c]pyridin-7-yl-N-methyl-N-(2-naphthylmethyl)-4-piperidinamine A solution of 700 mg of the product obtained in Step A in 20 ml of tetrahydrofuran is added at 0° C. to a suspension of 123 mg of $LiAlH_4$ in 20 ml of tetrahydrofuran. The whole is stirred for 3 hours at ambient temperature and then hydrolysed with 0.17 ml of water, 0.5 ml of 20% sodium hydroxide solution and 0.70 ml of water. The whole is filtered, evaporated and purified by chromatography on silica gel (dichloromethane/ethanol: 95/5), enabling the expected product to be isolated.

Melting point: 125–127° C. (M.K.).

EXAMPLE 4

N-(2-Naphthylmethyl)-1-thieno[2,3-c]pyridin-7-yl-4-piperidinamine Fumarate

The procedure is as in Example 1, using as substrate 7-chlorothieno[2,3-c]pyridine.

Melting point: 186–192° C. (M.K.).

EXAMPLE 5

N-(2-Naphthylmethyl)-1-furo[3,2-c]pyridin-4-yl-4-piperidinamine Hemi-fumarate

The procedure is as in Example 1, using as substrate 4-chlorofuro[3,2-c]pyridine.

Melting point: 194–197° C. (M.K.).

EXAMPLE 6

N-(2-Naphthylmethyl)-1-thieno[3,2-c]pyridin-4-yl-4-piperidinamine Hemi-fumarate

The procedure is as in Example 1, using as substrate 4-chlorothieno[3,2-c]pyridine.

Melting point: 208–212° C. (M.K.).

EXAMPLE 7

4-{1-[2-(1-Naphthyl)ethyl]-4-piperidinyl}furo[3,2-c]pyridine and its fumarate

Step A: 1-(4-Furo[3,2-c]pyridin-4-yl-1-piperidinyl)-2-(1-naphthyl)-1-ethanone 5.4 mmol of carbonyldiimidazole are added to a solution of 0.92 g of 1-naphthylacetic acid in 30 ml of dichloromethane. After 2 hours at ambient temperature, 1 g of the compound of Preparation 7 in 20 ml of dichloromethane is added. The expected product is isolated by hydrolysis, extraction, drying and concentration under reduced pressure.

Melting point: 50° C. (B.K.).

Step B: 4-{1-[2-(1-Naphthyl)ethyl]-4-piperidinyl}furo[3,2-c]pyridine and its Fumarate A solution of 1.4 g of the product obtained in the above Step A in 50 ml of tetrahydrofuran is introduced into a suspension of 215 mg of LiAlH$_4$ in 20 ml of tetrahydrofuran. After 2 hours at ambient temperature, the whole is hydrolysed with 2 ml of water and dissolved in 10 ml of tetrahydrofuran, insoluble material is filtered off, and the filtrate is evaporated and taken up in ether, washed with water, dried over MgSO$_4$, filtered and evaporated, enabling the expected product to be isolated; the product is converted into the fumarate.

Melting point (fumarate): 224–226° C. (M.K.).

EXAMPLE 8

4-{1-[2-(2-Naphthyl)ethyl]-4-piperidinyl}furo[3,2-c]pyridine

The procedure is as in Example 7, Steps A and B, using 2-naphthylacetic acid in Step A.

Melting point: 96–97° C. (M.K.).

EXAMPLE 9

4-{4-[2-(Benzofuran-2-yl)ethyl]-1-piperazinyl}furo[3,2-c]pyridine

The procedure is as in Example 7, Steps A and B, using as substrates in Step A 2-benzo-furanylacetic acid and the product obtained in Preparation 3.

Melting point: 99–100° C. (M.K.).

EXAMPLE 10

4-{4-[2-(1H-Indol-5-yl)ethyl]-1-piperazinyl}furo[3,2-c]pyridine

The procedure is as in Example 7, Steps A and B, using as substrates in Step A 1H-indol-5-ylacetic acid and the product obtained in Preparation 3.

Melting point: 153–156° C. (M.K.).

EXAMPLE 11

4-4-{4-[2-(2,3-Dihydrobenzofuran-5-yl)ethyl]-1-piperazinyl}furo[3,2-c]pyridine

The procedure is as in Example 7, Steps A and B, using as substrates in Step A 2,3-dihydro-1-benzofuran-5-ylacetic acid and the product of Preparation 3.

Melting point: 105–107° C.

EXAMPLE 12

7-{4-[2-(Benzofuran-2-yl]ethyl[-1-piperazinyl}furo[2,3-c]pyridine

The procedure is as in Example 7, Steps A and B, using as substrates in Step A benzofuran-2-ylacetic acid and the product obtained in Preparation 5.

Melting point: 111–113° C. (M.K.).

EXAMPLE 13

7-{4-[2-(Benzofuran-2-yl)ethyl]-1-piperazinyl}thieno[2,3-c]pyridine

The procedure is as in Example 7, Steps A and B, using as substrates in Step A benzofuran-2-ylacetic acid and the product obtained in Preparation 4.

Melting point: 97–98° C. (M.K.).

EXAMPLE 14

4-{1-[2-(1-Naphthyl)ethyl]-4-piperidinyl}thieno[3,2-c]pyridine and its Hydrochloride The procedure is as in Example 7, Steps A and B, using as substrate in Step A the product of Preparation 8.

Melting point (dihydrochloride): 256–260° C. (M.K.).

EXAMPLE 15

4-{4-[2-(Benzofuran-2-yl)ethyl]-1-piperazinyl}thieno[3,2-c]pyridine

The procedure is as in Example 7, Steps A and B, using as substrates in Step A benzofuran-2-ylacetic acid and the product obtained in Preparation 6.

Melting point: 99–100° C. (M.K.).

EXAMPLE 16

4-{4-[2-(2,3-Dihydro-1,4-benzodioxin-2-yl)ethyl]-1-piperazinyl}thieno[3,2-c]pyridine and its Hydrochloride The procedure is as in Example 7, Steps A and B, using as substrates in Step A 2,3-dihydro-1,4-benzodioxin-2-ylacetic acid and the product obtained in Preparation 6.

Melting point (dihydrochloride): 140–145° C. (M.K.).

EXAMPLE 17

7-[4-(2H-Chromen-3-ylmethyl)-1-piperazinyl]-1H-pyrrolo[2,3-c]pyridine 1.45 g of sodium triacetoxyborohydride and 0.3 ml of acetic acid are added at ambient temperature to a solution of 0.8 g of 2H-chromen-3-ylcarbaldehyde and 1 g of the product obtained in Preparation 12 in 100 ml of dichloromethane. After 24 hours, the reaction mixture is rendered alkaline by the addition of 20% sodium hydroxide solution, extracted with dichloromethane, dried, evaporated and purified by chromatography on silica gel (dichloromethane/ethanol: 95/5), enabling the expected product to be isolated.

Melting point: 165–169° C. (M.K.).

EXAMPLE 18

7-[4-(Chroman-4-ylmethyl)-1-piperazinyl]-1H-pyrrolo[2,3-c]pyridine

The procedure is as in Example 17, using as substrate chroman-4-ylcarbaldehyde.

Melting point: 228–231° C. (M.K.).

EXAMPLE 19

7-{4-[2-(Chroman-4-yl)ethyl]-1-piperazinyl}-1H-pyrrolo[2,3-c]pyridine

The procedure is as in Example 17, using as substrate chroman-4-ylacetaldehyde.

Melting point: 244–247° C. (M.K.).

EXAMPLE 20

4-{4-[2-(1-Naphthyl)ethyl]-1-piperazinyl}furo[3,2-c]pyridine

A solution of 50 ml of acetone, 1.5 g of 2-(naphth-1-yl)-1-bromoethane, 1.1 g of the product of Preparation 3 and 1.5 g of potassium carbonate is heated at reflux for 24 hours. The solution is diluted with water, extracted with ether and extracted with 1N hydrochloric acid and the acidic aqueous phase is rendered alkaline with 10% sodium hydroxide solution. After extraction of the basic phase with methylene chloride, the extract is dried, evaporated and crystallised from ether, enabling the expected product to be isolated.

Melting point: 94–98° C. (M.K.).

EXAMPLE 21

4-{4-[2-(2-Naphthyl)ethyl]-1-piperazinyl}furo[3,2-c]pyridine

The procedure is as in Example 20, using as substrate 2-(naphth-2-yl)-1-bromoethane.

Melting point: 113–115° C. (M.K.).

EXAMPLE 22

4-{4-[3-(Benzofuran-2-yl)propyl]-1-piperazinyl}furo[3,2-c]pyridine and its Dihydrochloride The procedure is as in Example 20, using as substrate 2-(3-bromopropyl)benzofuran.

Melting point (dihydrochloride): 194–197° C. (M.K.).

EXAMPLE 23

N-(2-Naphthylmethyl)-N-[1-(1H-pyrrolo[2,3-c]pyridin-7-yl)-4-peridinyl]amine

The procedure is as in Example 20, using as substrates 2-(α-bromomethyl)naphthalene and the product obtained in Preparation 13.

Melting point: 171–173° C. (M.K.).

EXAMPLE 24

7-{4-[(2-Naphthylmethyl)amino]-1-piperidinyl}-1,3-dihydro-2H-pyrrolo[2,3-c]pyridin-2-one The procedure is as in Example 20, using as substrates 2-(α-bromomethyl)naphthalene and the product obtained in Preparation 11.

Melting point: 186–190° C. (M.K.).

EXAMPLE 25

7-{4-[2-(2-Naphthyl)ethyl]-1-piperazinyl}-1,3-dihydro-2H-pyrrolo[2,3-c]pyridin-2-one The procedure is as in Example 20, using as substrates 2-(naphth-2-yl)-1-bromoethane and the product obtained in Preparation 10.

Melting point: 184–186° C. (M.K.).

EXAMPLE 26

7-{4-[2-(2-Naphthyl)ethyl]-1-piperazinyl}-1H-pyrrolo[2,3-c]pyridine

The procedure is as in Example 20, using as substrates 2-(naphth-2-yl)-1-bromoethane and the product obtained in Preparation 12.

Melting point: 149–151IC (M.K.).

EXAMPLE 27

7-{4-[2-(1-Naphthyl)ethyl]-1-pierazinyl}-1H-pyrrolo[2,3-c]pyridine

The procedure is as in Example 20, using as substrate the product obtained in Preparation 12.

Melting point: 169–172° C. (M.K.).

EXAMPLE 28

3-{2-[4-(1H-Pyrrolo[2,3-c]pyridin-7-yl)-1-piperazinyl]ethyl}1,3-benzoxazol-2(3H)-one The procedure is as in Example 20, using as substrates 3-(2-bromoethyl)-1,3-benzoxazol-2(3H)-one and the product of Preparation 12.

Melting point: 225–227° C. (M.K.).

EXAMPLE 29

7-{4-[2-(2H-Chromen-3-yl)ethyl-]1-piperazinyl}1H-pyrrolo[2,3-c]pyridine

The procedure is as in Example 20, using as substrate 2-(2H-chromen-3-yl)-1-bromoethane and the product of Preparation 12.

Melting point: 177–180° C. (M.K.).

EXAMPLE 30

7-{4-[2-(2-Naphthyl)ethyl]-1-piperazinyl}furo[2,3-c]pyridine and its Fumarate

The procedure is as in Example 20, using the product of Preparation 5.

Melting point (fumarate): 175–181° C. (M.K.).

EXAMPLE 31

7-[4-(2,3-Dihydro-1,4-benzodioxin-2-ylmethyl)-1-piperazine]thieno[2,3-c]pyridine and its Dihydrochloride The procedure is as in Example 20, using as substrates 2-(α-bromoethyl)-2,3-dihydro-1,4-benzodioxin and the product of Preparation 4.

Melting point (dihydrochloride): 195–200° C. (M.K.).

EXAMPLE 32

4-{1-[2-(1-Naphthyl)ethyl]4-piperidinyl}-1H-pyrrolo[3,2-c]pyridine and its Hydrochloride The procedure is as in Example 20, using as substrate the product of Preparation 15.

Melting point (hydrochloride): 180–185° C. (M.K.).

EXAMPLE 33

4-(4-{2-[5-(1,2,4-Triazol-1-ylmethyl)-1H-indol-3-yl]ethyl}-1-piperazinyl)furo[3,2-c]pyridine and its Trihydrochloride The procedure is as in Example 20, using 2-[5-(1,2,4-triazol-1-ylmethyl)-1H-indol-3-yl])-1-bromoethane instead of 2-(naphth-1-yl)-1-bromoethane.

Melting point (trihydrochloride): 196–200° C. (M.K.).

EXAMPLE 34

4-(4-{2-[5-(1,2,4-Triazol-1-ylmethyl)-1H-indol-3-yl]ethyl}-1-piperazinyl)-1H-pyrrolo[3,2-c]pyridine and its Dihydrochloride The procedure is as in Example 20, using as substrates the product of Preparation 14 and 2-[5-(1,2,4-triazol-1-ylmethyl)-1H-indol-3-yl]-1-bromoethane.

Melting point (dihydrochloride): 205–210° C. (M.K.).

EXAMPLE 35

1-[2-(4-Furo[3,2-c]pyridin-4-yl-1-Piperazinyl)ethyl]-1,3-dihydro-2H-benzimidazol-2-one Step A: 1-[2-(4-Furo[3,2-c]pyridin-4-yl-1-piperazinyl)ethyl]-3-(1-phenylvinyl)-1,3-dihydro-2H-benzimidazol-2-one The procedure is as in Example 20, using as substrate 1-(2-bromoethyl)-3-(1-phenylvinyl)-1,3-dihydro-2H-benzimidazol-2-one.

Step B: 1-[2-(4-Furo[3,2-c]pyridin-4-yl-1-piperazinyl) ethyl]-1,3-c]-dihydro-2H-benzimidazol-2-one A mixture formed from 1.7 g of the product obtained in Step A of this Example, 5 ml of concentrated hydrochloric acid and 20 ml of water is heated at 65° C. for 30 minutes. After cooling, the reaction mixture is washed with ether, rendered basic to pH 9–10 by the addition of potassium carbonate and then extracted with ether. The expected product is obtained by drying and purification by chromatography on silica gel.

Melting point: 152–154° C. (M.K.).

EXAMPLE 36

1-[2-(4-Thieno[3,2-c]pyridin-4-yl-piperazinyl) ethyl]-1,3-dihydro-2H-benzimidazol-2-one The procedure is as in Example 35, Steps A and B, using in Step A the product of Preparation 6.

Melting point: 215–220° C. (M.K.).

EXAMPLE 37

4-{4-[N-Naphth-2-ylmethyl)-N-(2-hydroxyethyl) amino]-4-piperidinyl}thieno[3,2-c]pyridine Step A: Ethyl {N-(naphth-2-ylmethyl)-N-[1-(thieno[3,2-c] pyridin-4-yl)]4-piperidinyl}-aminoacetate A mixture formed from 2.6 g of the product obtained in Example 6, 1 ml of ethyl bromoacetate, 2,3 g of potassium carbonate and 50 ml of acetonitrile is stirred at ambient temperature for 12 hours and then filtered and concentrated under reduced pressure, enabling the expected product to be obtained.

Step B: 4-{4-[N-(Naphth-2-ylmethyl)-N-(2-hydroxyethyl) amino]-4-piperidinyl}-thieno[3,2-c]pyridine A solution of 4 g of the product obtained in Step A in 100 ml of tetrahydrofuran is poured at 0° C. into a suspension of 0.43 g of lithium aluminium hydride in 60 ml of tetrahydrofuran. After 30 seconds at that temperature, 0.86 g of lithium aluminium hydride is added and the reactants are left in contact for a further 15 minutes. Hydrolysis is subsequently carried out with 0.6 ml of water and then 0.5 ml of 20% sodium hydroxide solution. The whole is filtered, concentrated and purified by chromatography on silica (ethyl acetate) to obtain the expected product.

Melting point: 53–55° C. (M.K.).

EXAMPLE 38

4-{4-[2-(Isochroman-1-yl)ethyl]-1-piperazinyl}thieno[3,2-c]pyridine and its Dihydrochloride 12.3 mM of mesyl chloride dissolved in 10 ml of dichloromethane are added at 0° C. to a solution of 11.2 mM of 2-(isochroman-1-yl)ethanol and 1.24 g of triethylamine in 10 ml of dichloromethane. After stirring the mixture for two hours at ambient temperature, 16.8 mM of the product of Preparation 6 suspended in 30 ml of dichloromethane are added, and then the reaction mixture is heated at reflux and 35 ml of ethylene glycol are added while distilling off the dichloromethane. After 3 hours at 80° C., the reaction is continued for 12 hours at ambient temperature. The reaction mixture is then poured into 200 ml of water and extracted with ethyl acetate. The combined organic phases are washed with water, dried, filtered and then concentrated under reduced pressure. Chromatography of the residue on silica gel (ethyl acetate) enables the expected product to be isolated in the form of an oil, which is converted into the dihydrochloride by the action of ethereal hydrogen chloride.

Melting point: 146–148° C. (M.K.).

EXAMPLE 39

4-(4-{2-[5-(Imidazol-1-ylmethyl)1H-indol-3-yl] ethyl}-1-piperazinyl)-1H-pyrrolo[3,2-c]-pyridine Step 1: 2-(5-Bromo-1H-indol-3-yl)ethanol A solution of 6 g of N-tert-butoxycarbonyl-5-bromo-3-ethoxycarbonylmethylindole in 50 ml of tetrahydrofuran is added dropwise to a suspension, cooled to 0° C., of 0.9 g of LiAlH$_4$ in 35 ml of tetrahydrofuran. After stirring for 20 hours at ambient temperature, the mixture is cooled to 0° C. and then treated in succession with 0.9 ml of water, 3,2 ml of an aqueous 20% sodium hydroxide solution and 3.6 ml of water. After filtration and concentration of the filtrate in vacuo, the residue is chromatographed on silica gel (dichloromethane/ethyl acetate: 90/10), enabling the expected product to be isolated.

Melting point: 85–89° C.

Step 2: 2-(5-Bromo-1H-indol-3-yl)-1-bromoethane

A solution of 11.5 g of triphenylphosphine in 60 ml of dichloromethane is added to a solution, cooled to 0° C., of 4 g of the compound obtained in Step 1 and 7.5 g of carbon tetrabromide in 100 ml of dichloromethane. After stirring for 48 hours at ambient temperature, the reaction mixture is concentrated in vacuo. The residue obtained is chromatographed on silica gel (dichloromethane/cyclohexane: 80/20), enabling the expected product to be isolated.

Melting point: 65–70° C.

Step 3: 4-{4-[2-(5-Bromo-1H-indol-3-yl)ethyl]-1-piperazinyl}-1H-pyrrolo[3,2-c]pyridine The procedure is as in Example 20, using as substrates the product obtained in Step 2 and the product of Preparation 14.

Melting point: 112–115° C. (M.K.).

Step 4: 3-{2-[4-(1H-Pyrrolo[3,2-c]pyridin-4-yl)-1-piperazinyl]ethyl}-1H-indol-5-carbaldehyde A solution at −78° C. of 1.5 mmol of the compound obtained in Step 3 in tetrahydrofuran is treated with 9 mmol of tert-butyllithium (1.8M in hexane). After stirring the mixture for 1 hour, 12 mmol of dimethylformamide are added and the mixture is brought to ambient temperature. After reaction for 4 hours, the solution is hydrolysed by a saturated solution of NH$_4$Cl and then extracted with dichloromethane. After treating the organic phase in conventional manner, chromatography of the residue on silica gel enables the expected product to be isolated.

Step 5: 4-{4-[2-(5-Hydroxymethyl-1H-indol-3-yl)ethyl]-piperazinyl}-1H-pyrrolo[3,2-c]pyridine A solution of 2 mmol of the compound obtained in Step 4 in 50 ml of ethanol is treated with 2.2 mmol of sodium borohydride for 24 hours. The solvent is evaporated off under reduced pressure and the residue obtained is taken up in water and then extracted with dichloromethane. The organic phase is dried and filtered and then concentrated under reduced pressure, enabling the expected product to be obtained.

Step 6: 4-{4-[2-(5-Bromoethyl-1H-indol-3-yl)ethyl]-1-Piperazinyl}-1H-pyrrolo[3,2-c]pyridine The procedure is as in Step 2 of this Example, using as substrate the product obtained in Step 5.

Step 7: 4-(4-{2-[5-(Imidazol-1-ylmethyl)-1H-indol-3-yl] ethyl}-1-piperazinyl)-1H-Pyrrolo[3,2-c]pyridine A solution of 3.7 mmol of the compound obtained in Step 6 and 4.1 mmol of tritylimidazole in 50 ml of acetonitrile is heated at reflux for 24 hours and then heated at 60° C. for 24 hours in the presence of 50 ml of methanol. The reaction mixture is then concentrated in vacuo. The residue is taken up in a 5/1 biphasic mixture: dichloromethane/ 20% sodium hydroxide solution. The organic phase is dried, filtered and concentrated under reduced pressure, enabling the expected product to be obtained.

EXAMPLE 40

4-(4-{2-[5-(1H-Imidazol-5-ylmethyl)-1H-indol-3-yl] ethyl}-1-piperazinyl)-1H-pyrrolo[3,2-c]pyridine Step 1: (3-{2-[4-(1H-Pyrrolo[3,2-c]pyridin-4-yl)-1-piperazinyl]ethyl}-1H-indol-5-yl)-(1-trityl-1H-imidazol-4-yl)methanol At ambient temperature, a 3M solution of 2.2 mmol of ethylmagnesium bromide and then, after 30 minutes, 2.2 mmol of the compound obtained in Step 4 of Example 39, are added to a solution of 2.0 mmol of 4-iodo-1-tritylimidazole in dichloromethane (0.25M). After stirring for 18 hours, the mixture is treated with a saturated solution of $NH_4Cl$ and then extracted with dichloromethane, and the organic phase is treated in conventional manner. Chromatography on silica gel enables the expected product to be isolated.

Step 2: 4-(4-{2-[5-(1H-Imidazol-5-ylmethyl)-1H-indol-3-yl]ethyl}-1-piperazinyl)-1H-pyrrolo[3,2-c]pyridine A solution, cooled to −5° C., of 1.9 mmol of the compound obtained in Step 1 and 9.5 mmol of triethylsilane in dichloromethane, is treated with a solution of 19 mmol of trifluoroacetic acid. After stirring at ambient temperature for 18 hours, the reaction mixture is treated with a saturated solution of $NaHCO_3$, and then the organic phase is treated with a 2N HCl solution. The aqueous phase is rendered basic with 20% sodium hydroxide solution, and extraction with dichloromethane enables the expected product to be isolated after drying and concentrating the organic phase.

PHARMACOLOGICAL STUDY OF THE COMPOUNDS OF THE INVENTION

A. In vitro study

EXAMPLE 41

Determination of the Affinity for Serotonin Reuptake Sites

The affinity was determined by competition experiments using [$^3$H]-paroxetine (NEN, Les Ulis, France). The membranes are prepared from rat frontal cortex and are incubated in triplicate for 2 hours at 25° C. with 1.0 nM [$^3$H]-paroxetine and cold ligand in a final volume of 0.4 ml. The incubation buffer contains 50 nM TRIS-HCl (pH 7.4), 120 mM NaCl and 5 mM KCl. The non-specific binding is determined using 10 μM citalopram. At the end of the incubation, the incubation medium is filtered and washed three times with 5 ml of cooled buffer. The radioactivity retained on the filters is determined by liquid scintillation counting. The binding isotherms are analysed by non-linear regression to determine the $IC_{50}$ values. Those values are converted into a dissociation constant ($K_i$) using the Cheng-Prusoff equation:

$$K_i = IC_{50}/(1+L/K_d)$$

wherein L is the concentration of [$^3$H]-paroxetine and $K_d$ is the dissociation constant of [$^3$H]-paroxetine from the serotonin reuptake site (0.13 nM). The results are expressed in $pK_i$.

The compounds of the present invention demonstrate very good affinity for serotonin reuptake sites. By way of example, the $pK_i$ of the compound of Example 7 is higher than 7.5.

EXAMPLE 42

Determination of the Affinity for 5-$HT_{1A}$ Receptors

The affinity was determined by competition experiments using [$^3$H]-8-OH-DPAT (NEN, Les Ulis, France). The membranes, prepared from CHO cells transfected with 5$HT_{1A}$ receptor, were prepared as described in *Neuropharmacol.*, 1997, 36, 451–459. The membranes were incubated in triplicate for two and a half hours at 25° C. with 0.4 nM [$^3$H]-8-OH-DPAT and cold ligand in a final volume of 1.0 ml. The incubation buffer contains 50 mM HEPES-NaOH (pH 7.4) and 5 mM $MgCl_2$. The non-specific binding is determined using 10 μM 5-HT. At the end of the incubation, the incubation medium is filtered through filters impregnated with 0.1% polyethyleneimine and washed three times with 5 ml of cooled buffer. The radioactivity retained on the filters is determined by liquid scintillation counting. The binding isotherms are analysed by non-linear regression to determine the $IC_{50}$ values. Those values are converted into a dissociation constant ($K_i$) using the Cheng-Prusoff equation:

$$K_i = IC_{50}/\{(1+L/K_d)-1\}$$

wherein L is the concentration of [$^3$H]-8-OH-DPAT and $K_d$ is the dissociation constant of [$^3$H]-8-OH-DPAT from the 5$HT_{1A}$ receptor (0.65 nM). The results are expressed in $pK_i$.

By way of example, and to illustrate the activity of the products of the invention, the $pK_i$ of the product of Example 7 is higher than 7.5.

B. In vivo study

EXAMPLE 43

Microdialysis Experiment in the Rat

Rats are anaesthetised with pentobarbital (60 mg/kg i.p.). They are placed in a Kopf stereotactic device and the cannula guide is implanted in the cingulate frontal cortex in accordance with the coordinates described in the Paxinos and Watson atlas (1982) as follows: AP=+2.2; L=±0.6; DV=−0.2. The rats are placed in separate cages and are not used in dialysis until 5 days later. On the day of the dialysis, the probe is slowly lowered and held in position. The probe is perfused at a flow rate of 1 μl/min. with a solution of 147.2 mM NaCl, 4 mM KCl and 2.3 mM $CaCl_2$ adjusted to pH 7.3 with a phosphate buffer (0.1 M). Two hours after implantation, samples are collected every 20 minutes for 4 hours. Three baseline samples are taken before administration of the products to be tested. The rats are left in their individual cages for the whole of the experiment. When the experiment is finished, the rats are decapitated and the brain is removed and frozen in isopentane. Sections of a thickness of 100 μm are cut and stained with cresyl violet, which allows verification of the location of the probes.

The simultaneous quantification of dopamine, norepinephrine and serotonin is carried out as follows: 20 μl dialysis samples are each diluted with 20 μl of mobile phase ($NaH_2PO_4$: 75 mM; EDTA: 20 M; sodium 1-decanesulphonate: 1 mM; methanol: 17.5%; triethylamine: 0.01%; pH: 5.7) and 33 μl samples are analysed by HPLC using a reverse phase column thermostatically maintained at 45° C. and quantified by means of a coulometric detector. The potential of the first electrode of the detector is set at −90 mV (reduction) and that of the second at +280 mV (oxidation). The mobile phase is injected at a flow rate of 2 ml/min using a Beckman 116 pump. The sensitivity limits for dopamine, norepinephrine and serotonin are 0.55 fmol per sample. All the products of the invention are injected subcutaneously in a volume of 1.0 ml/kg. The products are dissolved in distilled water to which a few drops of lactic acid have been added if necessary.

Results:

By way of example, and in order to illustrate the activity of the products of the invention, the compound of Example 7, administered subcutaneously at a dose of 10 mg/kg, increases the level of serotonin by: 140.5±15.2% (maximum % of the effect compared with the baseline level defined as 0%).

EXAMPLE 44

Test of Aggressiveness in Isolated Mice

This test allows the evaluation of the intraspecies anti-aggressive activity of a product in mice that have been kept in isolation for several months.

Animals:

The test uses male CD mice (Charles River) weighing from 22 to 25 g. On their arrival, the animals are isolated in individual opaque black cages (23×14×13 cm) with a grill lid, and are housed for a prolonged period (approximately six months) in the experimentation room.

Selection of Pairs of Mice

The selection of aggressive pairs of mice that will be used for an extended period in the study commences after the animals have been isolated for one month. Once or twice per week a mouse from another cage (intruder) is placed in the cage of a (resident) mouse and the two animals are observed to see if they attack one another (sniffing, pursuing, nibbling, biting) during that trial. At the end of the trial (maximum duration 10 minutes), each mouse is isolated again in its own cage. If attacks have occurred, the same pair will be tested again in the next trial; if there have been no attacks, each mouse of that pair will be placed in the presence of another mouse in the subsequent trial. Thus, in the course of successive trials carried out at a rate of 1 or 2 per week, definitive pairs of mice that will be used for the experiments are selected. The selection of the pairs is based on the stability of the combative nature of the animals from one trial to the next, the shortness of the latent period of the first attack and the frequency and duration of the attacks. With the pairs selected in that manner, those parameters are checked each week by a rapid trial, without treatment, two days before the test day.

Test:

The test takes place once a week. 30 minutes before being placed together, the two mice of the pair each receive the same treatment (product or solvent) and remain isolated in their respective cages. At T0., the intruder mouse is introduced into the cage of the resident mouse for a period of 3 minutes. The latent period (in seconds) of the first attack and the number and total duration (in seconds) of the attacks are recorded. Any reversal in the dominance of one mouse in relation to the other is also noted (in general, the resident mouse is the dominant mouse).

At the end of the test, the intruder mouse returns to its cage; the animals remain in isolation until the next rapid trial and test the following week.

Results:

By way of example, and in order to illustrate the activity of the products of the invention, the Inhibitory Dose 50 for the compound of Example 7 is less than 1.5 mg/kg i.p.

EXAMPLE 45

Marble-burying Test in Mice

This test enables evaluation of the capacity of pharmacological agents to inhibit the spontaneous marble-burying behaviour of mice, the inhibition being predictive of anti-depressant and/or anti-impulsive action. Male mice of the NMRI strain (Iffa-Credo, l'Arbresle, France) weighing from 20 to 25 g on the day of the experiment are placed individually in Macrolon boxes (30×18×19 cm) containing 5 cm of sawdust and covered with a perforated plexiglass plate. Twenty four "tiger's eye" glass marbles are evenly distributed on the sawdust at the periphery of the box. At the end of 30 minutes' free exploration, the animals are removed from the box and the number of buried marbles is counted.

Results:

By way of Example, the following Table shows the effects of the products of the invention compared with the effect of fluoxetine, a reference antidepressant

| Example | Marble-burying in mice, $ID_{50}$ |
|---|---|
| fluoxetine | 8.03 |
| 7 | 1.64 |
| 11 | 0.94 |

$ID_{50}$ = inhibitory dose$_{50}$

The doses are expressed in mg/kg s.c.

EXAMPLE 46

Pharmaceutical Composition: Tablets formulation for the preparation of 1000 tablets each comprising 5 mg of active ingredient:

| | |
|---|---|
| compound of Example 7 | 5 g |
| hydroxypropyl methylcellulose | 5 g |
| wheat starch | 10 g |
| lactose | 100 g |
| magnesium stearate | 2 g |

What is claimed is:

1. A compound selected from those of formula (I):

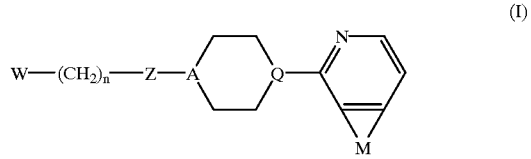

wherein:

W represents:
either naphthyl optionally substituted by one or more identical or different groups selected from halogen, linear or branched ($C_1$–$C_6$)alkyl, hydroxy, linear or branched ($C_1$–$C_6$)alkoxy, cyano, nitro, linear or branched trihalo($C_1$–$C_6$)alkyl, methylenedioxy, and ethylenedioxy,
or a group selected from 2,3-dihydro-1,4-benzodioxinyl, chromanyl, 2H-chromenyl, isochromanyl, 2,3-dihydrobenzofuranyl, benzofuranyl, and 2-oxo-1,3-benzoxazol-3(2H)-yl and each of the groups being optionally substituted by one or more identical or different groups selected from halogen, hydroxy, cyano, nitro, oxo, linear or branched ($C_1$–$C_6$)alkyl, linear or branched ($C_1$–$C_6$) alkoxy, linear or branched trihalo($C_1$–$C_6$)alkyl, heterocycloalkylalkylene in which alkylene has from 1 to 6 carbon atoms and may be linear or branched and in which heterocycloalkyl is imidazolyl or triazolyl, or a group selected from indolyl and 2-oxo-2,3-dihydro-1H-benzimidazol-1-yl, n represents an integer from 2 to 3 inclusive, Z represents a single bond, A represents nitrogen, Q represents nitrogen, M, together with the carbon of pyridyl to which it is bonded, represents thieno, furo, pyrrolo or oxopyrrolo, which are fused [3,2-c] or [2,3-c] with the pyridinyl, and pharmaceutically-acceptable acid or base additional salts thereof, it being understood that "aryl" is phenyl, naphthyl, dihydronaphthyl, or tetrahydronaphthyl.

2. A compound of claim 1 wherein, when W is substituted by heterocycloalkylalkylene, wherein the alkylene moiety is a linear or branched ($C_1$–$C_6$)alkylene, the heterocycloalkylatkylene is a heterocycloalkylmethylene group in which the heterocycloalkyl ring is imidazolyl or triazolyl.

3. A compound of claim 2, wherein W is substituted by a heterocycloalkylmethylene group selected from 1,2,4-triazol-1-ylmethyl, imidazol-1-ylmethyl, and 1H-imidazol-5-ylmethyl.

4. A compound of claim 1, wherein W represents a group selected from 1-naphthyl, isochroman-1-yl, and 2,3-dihydrobenzofuran-5-yl.

5. A compound of claim 1, wherein W represents a group selected from 1,3-benzoxazol-2-on-1-yl, and 1,3-dihydro-2H-benzimidazol-2-on-1-yl.

6. A compound of claim 1, wherein M, together with the carbon of the pyridinyl to which it is bonded, represents thieno or furo.

7. A compound of claim 1 which is 4-{4-[2-(2,3-dihydrobenzofuran-5-yl)ethyl]-1-piperazinyl}furo[3,2-c]pyridine, and pharmaceutically-acceptable acid or base addition salts thereof.

8. A compound of claim 1 which is 4-{4-[2-(isochroman-1-yl)ethyl]-1-piperazinyl}thieno[3,2-c]pyridine, and pharmaceutically-acceptable acid or base addition salts thereof.

9. A compound of claim 1 which is selected from 1-[2-(4-furo[3,2-c]pyridin-4-yl-1-piperazinyl)ethyl]-1,3-dihydro-2H-benzimidazol-2-one, and 1-[2-(4thieno[3,2-c]pyridin-4-yl-1-piperazinyl)ethyl]-1,3-dihydro-2H-benzimidazol-2-one, and pharmaceutically-acceptable acid or base addition salts thereof.

10. A method for treating a living body afflicted with a disease selected from depression, anxiety, panic attacks, obsessive-compulsive disorders, phobias, and impulsive disorders, comprising the step of administering to the living body an amount of a compounds of claim 1 which is effective for alleviation of the disease.

11. A pharmacological composition useful in treating a living body afflicted with a disease selected from depression, anxiety, panic attacks, obsessive-compulsive disorders, phobias, and impulsive disorders, comprising as active principle an effective amount of a compound of claim 1, together with one or more pharmaceutically-acceptable excipients or vehicles.

12. A method of treating a living body afflicted with a disease selected from depression, anxiety, panic attacks, obsessive-compulsive disorders, phobias, and impulsive disorders, comprising as active principle an effective amount of a compound selected from those of formula (I):

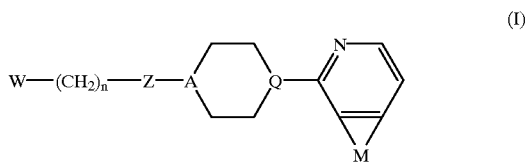

(I)

wherein:

W represents:
  indolyl or 2-oxo-2,3-dihydro-1H-benzimidazol-1-yl and each of the groups being optionally substituted by one or more identical or different groups selected from halogen, hydroxy, cyano, nitro, oxo, linear or branched ($C_1$–$C_6$)alkyl, linear or branched ($C_1$–$C_6$) alkoxy, linear or branched trihalo($C_1$–$C_6$)alkyl, heterocycloalkylalkylene in which alkylene has from 1 to 6 carbon atoms and may be linear or branched, and in which heterocycloalkyl is imidazolyl or triazolyl, n represents an integer from 2 to 3 inclusive, Z represents a single bond, A represents nitrogen, Q represents nitrogen, M, together with the carbon of pyridyl to which it is bonded, represents thieno, furo, pyrrolo or oxopyrrolo, which are fused [3,2-c] or [2,3-c] with the pyridinyl, and pharmaceutically-acceptable acid or base additional salts thereof, it being understood that "aryl" is phenyl, naphthyl, dihydronaphthyl, or tetrahydronaphthyl, which is effective for alleviation of the disease.

* * * * *